US005446149A

United States Patent [19]

Rickwood et al.

[11] Patent Number: 5,446,149

[45] Date of Patent: Aug. 29, 1995

[54] BRIDGED SPIROXAZINE PHOTOCHROMIC COMPOUNDS

[75] Inventors: Martin Rickwood, Southport; Sean D. Marsden, Windle, both of United Kingdom

[73] Assignee: Pilkington plc, St. Helens, United Kingdom

[21] Appl. No.: 160,169

[22] Filed: Dec. 2, 1993

[30] Foreign Application Priority Data

Dec. 3, 1992 [GB] United Kingdom ................ 9225348

[51] Int. Cl.$^6$ .................................... C07D 265/14

[52] U.S. Cl. .................................... 544/71; 252/586

[58] Field of Search .................................... 544/71

[56] References Cited

U.S. PATENT DOCUMENTS

| | | | |
|---|---|---|---|
| 4,913,544 | 4/1990 | Rickwood et al. | 351/163 |
| 4,931,219 | 6/1990 | Kwiatkowski et al. | 252/586 |
| 4,968,454 | 11/1990 | Crano et al. | 252/586 |
| 5,017,698 | 5/1991 | Machida et al. | 544/71 |
| 5,114,621 | 5/1992 | Guglielmetti et al. | 252/586 |
| 5,139,707 | 8/1992 | Guglielmetti et al. | 252/586 |

FOREIGN PATENT DOCUMENTS

| | | |
|---|---|---|
| 0146135 | 6/1985 | European Pat. Off. . |
| 0141407 | 6/1988 | European Pat. Off. . |
| 0294056A2 | 12/1988 | European Pat. Off. . |
| 0245020B1 | 10/1991 | European Pat. Off. . |
| 0449669A1 | 10/1991 | European Pat. Off. . |
| 2049297 | 3/1971 | France . |
| 1310918 | 3/1973 | United Kingdom . |
| 1515641 | 6/1978 | United Kingdom . |
| 1515642 | 6/1978 | United Kingdom . |
| 2190088 | 12/1989 | United Kingdom . |
| WO85/02619 | 6/1985 | WIPO . |
| WO87/00524 | 1/1987 | WIPO . |

OTHER PUBLICATIONS

European Search Report EP 93 30 9416, dated Feb. 15, 1994.

C. B. McArdle, "*Applied Photochromic Polymer Systems*", 1992, Chapter 2, pp. 33–34.

Alan R. Katritzky and Kunihiko Akutagawa, "*A Practical Synthetic Method For N-Methyl-o-Toluidine*", OPPI Briefs, vol. 21, No. 3, 1989, pp. 340–341.

Alan R. Katritzky, Stanislaw Rachwal and Bogumila Rachwal, "*The Chemistry of Benzotriazole, Part 3.*[1] *The Aminoalkylation of Benzotriazole*", J. Chem. Soc. Perkin Trans. 1, 1987, pp. 799–804.

Louis F. Fieser, "*β-Naphthoquinone and α-Naphthoquinone*", Organic Synthesis 1937, 17, pp. 68–72.

(List continued on next page.)

*Primary Examiner*—Mukund J. Shah
*Assistant Examiner*—Matthew V. Grumbling
*Attorney, Agent, or Firm*—Burns, Doane, Swecker & Mathis

[57] ABSTRACT

Photochromic compounds having the following structure II

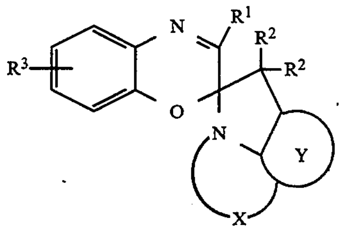

II in which $R^1$ is a group selected from hydrogen, alkyl, alkoxy, amino, aryl or heteroaryl;

each $R^2$ is a group selected from C1 to C10 branched or linear alkyls, carbocylic or heterocyclic, the $R^2$ groups can be independent or together from part of a carboxylic or heterocyclic ring;

$R^3$ is a group selected from hydrogen, alkyl, alkoxy, alkenyl, alkynyl, imino, azo, amino, carboxy ester, amide, cyano, halogen, trifluoromethyl, nitro, aryl or heteroaryl, $R^3$ is a fused carbocyclic or heterocyclic moiety;

Y is a six membered carbocyclic or heterocyclic ring.

X links N as shown to the ring Y to form a fused heterocyclic ring.

12 Claims, No Drawings

OTHER PUBLICATIONS

Katsuhira Yoshida, Tetsunao Koujiri, Norio Oga, Miwa Ishiguro and Yuji Kubo, "*The Effect of Metal Chelate Complexation on The Reactivity and Absorption Spectra of 1,2-Naphthoquinones: The Synthesis of New Types of Near I.r. Absorbing Dyes*", J. Chem. Soc., Chem. Commun., 1989, pp. 708–710.

Marshall Gates, "*The Condensation of Naphthoquinones With Polar Ethylenes*", from the Marian Edwards Park Laboratory of Bryn Mawr College, Jan. 1944, vol. 66, pp. 124–130.

BRIDGED SPIROXAZINE PHOTOCHROMIC COMPOUNDS

The present invention relates to photochromic compounds and articles such as ophthalmic lenses and windows including vehicle rooflights made from polymeric material in which the compounds are incorporated to confer photochromic properties on the polymeric material.

Organic photochromic compounds are compounds which are capable under the influence of actinic light of changing their structure and moving from a clear or faded state to a darkened state. The reversal from a darkened state to a faded or clear state occurs when the actinic light source is removed or reduced sufficiently in intensity to allow the reverse reaction which is primarily thermally induced to predominate. The photochromic behaviour of the known compounds is temperature dependent and, at low temperatures, return to the faded state may be so slow that e.g. a sunglass lens remains dark even though the wearer has moved into an area shaded from the sun, and at high temperatures, the thermal reversal reaction may predominate to such an extent that a wearer of a sunglass lens may not observe any darkening.

One way of overcoming this problem would be to adjust the concentration of photochromic compound in the polymeric material. However this is not a satisfactory solution for either the high or low temperature situation. In order to get a satisfactory darkening at high temperatures, the concentration must be increased which increases the cost, and the more material present there may be a problem with residual colour in the bleached or clear state.

On the other hand, at the low temperatures experienced by a lens, a reduction in concentration to try and reduce the time of fade from the darkened state would result in reduced darkening and the onset of fatigue would occur at an early stage in the life of the lens causing a noticeable loss of photochromic properties. Such a reduction would also mean that there would be insufficient darkening at the high end of the range.

We have found a new group of photochromic compounds making it possible to manufacture compounds whose induced optical density and in some cases fading rate has been adjusted to meet particular market requirements.

Thus by producing compounds in which the induced optical density has been increased by a structure modification, we can use less material, thus reducing the cost and the effect of residual colour in the bleached state. Reducing the induced optical density enables us to load more material to get sufficient darkening at low temperatures and an adequate life before fatigue makes the lens unusable.

We have found that in compounds where the structure includes a ring system as illustrated without substituents in (I), it is Possible to modify the structure to produce a desired change in induced optical density.

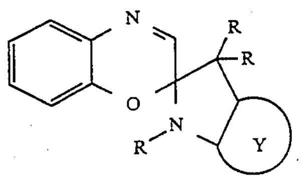

I

This is done by providing a linkage between the nitrogen atom in the pyrrolino ring and the carbocyclic or heterocyclic ring shown as Y. Y is a six membered ring.

According to the invention, there are provided new photochromic compounds having the following structure II

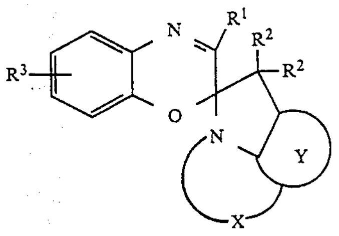

II in which $R^1$ is a group selected from hydrogen, alkyl, alkoxy or amino;

$R^2$ is a group selected from branched or linear-chain alkyl groups each containing from 1 to 10 carbon atoms, a carbocyclic group or a heterocyclic group, or together form a carboxylic or heterocyclic ring;

$R^3$ is a group selected from hydrogen, alkyl, alkoxy, alkenyl, alkynyl, imino, azo, amino, carboxy ester, amide, cyano, halogen, trifluoromethyl, nitro, substituted or unsubstituted phenyl, substituted or unsubstituted pyridyl or is a fused carbocyclic or heterocyclic moiety;

Y is a six membered carbocyclic or heterocyclic ring.

X links N as shown to the ring, said X-linkage containing from 2 to 4 carbon atoms Y to form a fused heterocyclic ring.

Preferred compounds in accordance with the invention include compounds having the structure III

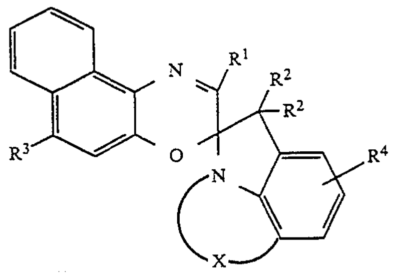

III in which $R^1$ is hydrogen;

$R^2$ is a group selected from branched or linear-chain alkyl groups containing from 1 to 10 carbon atoms, a carbocyclic ring or a heterocyclic ring or together form part of a carbocyclic or heterocyclic ring;

$R^3$ is a group selected from alkyl, substituted or unsubstituted phenyl, substituted or unsubstituted pyridyl, alkoxy, alkenyl, alkynyl, imino, axo, cyano, amino, halogen, trifluoromethyl and nitro;

$R^4$ is a group selected from alkyl, substituted or unsubstituted phenyl substituted or unsubstituted pyridyl, alkoxy, alkenyl, alkynyl, imino, azo, cyano, amino, halogen, trifluoromethyl and nitro, or $R^4$ is a carbocyclic or heterocyclic group fused to the 4, 5 or 5, 6 position of the indoline;

X links N as shown to the 7 position on the indoline ring to form a fused heterocyclic ring, said X-linkage containing 2 to 4 carbon atoms; Advantageously, $R^1$ is hydrogen;

$R^2$ is a branched or linear chain alkyl group containing from 1 to 10 carbon atoms;

$R^3$ is selected from the group consisting of hydrogen, a branched or linear alkyl group containing from 1 to 4 carbon atoms, an alkoxy group containing from 1 to 4 carbon atoms, an amino group, a halogen atom, a trifluoromethyl group, a substituted or unsubstituted phenyl group and an aryl substituted alkenyl group; and $R^4$ is selected from the group consisting of a branched or linear alkyl group containing from 1 to 4 carbon atoms, an alkoxy group containing from 1 to 4 carbon atoms, an amino group, a halogen atom, a trifluoromethyl group, a cyano group or a nitro group.

We have found that in the X linkage formed from between 2 and 4 carbon atoms, one or more of the carbon atoms may be substituted. A compound with the structure IV as shown below:

IV

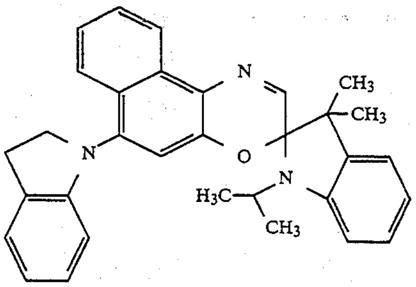

has a higher induced optical density than the compound V in which a 2 carbon linkage has been introduced into the molecule.

V

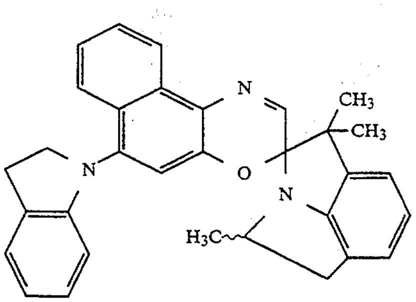

In the case of the compound with the structure VI shown below, a higher induced optical density than either IV or V is obtained.

VI

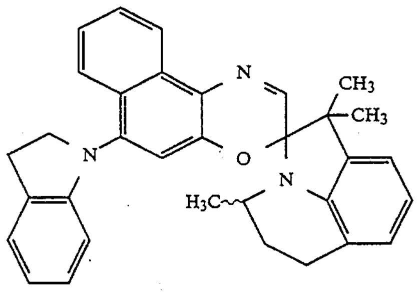

The effect of introducing a more bulky link is to cause the compound VI to have a higher induced optical density at 20° C. than the compound IV. It is believed that the smaller linkages cause strain when the molecule is in the open darkened form and increase the propensity for it to convert back to the ring closed clear state. This can be seen in Table I.

TABLE I

| | COMPOUND | | | | | |
|---|---|---|---|---|---|---|
| | IV | | V | | VI | |
| Time | IOD | % | IOD | % | IOD | % |
| ACTIVATION | | | | | | |
| 30 s | 0.606 | 86 | 0.359 | 79 | 0.711 | 72 |
| 1 min | 0.647 | 92 | 0.397 | 87 | 0.829 | 84 |
| 2 min | 0.674 | 96 | 0.425 | 93 | 0.909 | 92 |
| 5 min | 0.705 | 100 | 0.456 | 100 | 0.983 | 100 |
| FADE | | | | | | |
| 10 s | 0.424 | 40 | 0.289 | 37 | 0.790 | 20 |
| 20 s | 0.326 | 54 | 0.231 | 49 | 0.678 | 31 |
| 30 s | 0.272 | 61 | 0.195 | 57 | 0.606 | 38 |
| 40 s | 0.237 | 66 | 0.177 | 61 | 0.545 | 45 |
| 50 s | 0.211 | 70 | 0.161 | 65 | 0.499 | 49 |
| 1 min | 0.195 | 72 | 0.147 | 68 | 0.465 | 53 |
| 2 min | 0.135 | 81 | 0.108 | 76 | 0.345 | 65 |
| 5 min | 0.081 | 88 | 0.064 | 86 | 0.217 | 78 |

In the above table the Induced Optical Density has been determined under the following condition. 0.05% w/w material under test is cast in a 2.44 mm acrylic polymer illuminated at 20° C. under Air Mass 2. Further the activated state after 5 mins exposure is defined as the base state to which the other data is compared.

Considering the change to a darkened state, compound VI has the highest induced optical density after 5 minutes, with compound V less than compound IV. The percentage change with time shows that the change in induced optical density from clear to dark happens at about the same rate, but the change is taking place over a greater range in the case of compound VI.

The change to a faded state is similar in terms of rate of change for compounds IV and V, however, although compound VI starts darker than compound IV, it still fades at a slower rate than either IV or V.

The linkage can also include one or more nitrogen atoms.

For convenience, the examples of the form of the linkage are illustrated below as fragments of the spirooxazine molecule showing simply the indoline ring and the ring Y.

VII

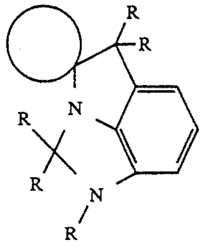

VIII

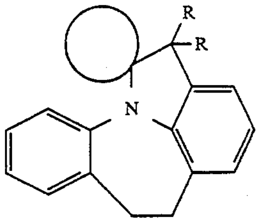

IX

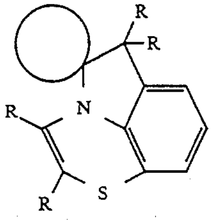

X

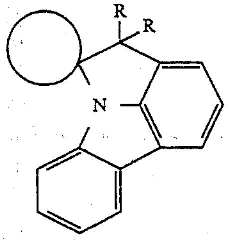

XI

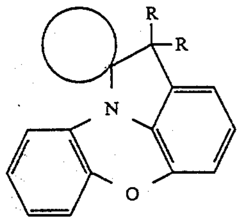

EXAMPLE 1

A mixture of 4-indolino-1-nitroso-2-naphthol (1.01 g;0.0035 mol) and 1,2,5,6-tetrahydro-1,1-dimethyl-2-methylene-4H-pyrrolo[3,2,1-ij]quinoline(0.73 g;0.0037 mol) in p-dioxan (30.0 ml) was heated under reflux for 24 h. The resulting solution was evaporated and the residue flash-chromatographed over silica (20% diethyl ether in hexane) to give a dark oil which was triturated with petrol ether (bp 40/60) to yield 1,2,5,6-tetrahydro-1,1,-dimethyl-6'-(2,3-dihydroindol-1-yl)spiro [4H-pyrrolo[3,2,1-ij]quinoline-2,3'-[3H]naphth[2,1-b][1,4]oxazine] as a green-yellow solid (0.51 g;30%). mp 185°-9° C.

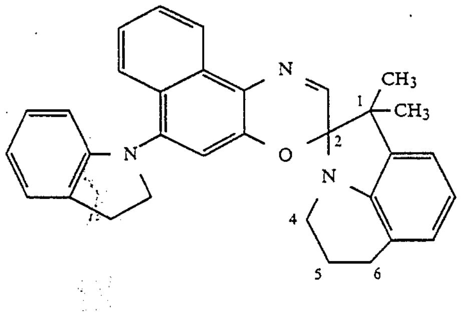

EXAMPLE 2

To a refluxing solution of 1-nitroso-2-naphthol (2.13 g;0.0123 mol) and piperidine (2.10 g;0.0246 mol) in trichloroethylene (25.0 ml) was added 1,2,5,6-tetrahydro-1,1-dimethyl-2-methylene-4H-[pyrrolo[3,2,1-ij]quinoline (2.44 g; 0.0123 mol) in one portion and the mixture heated for 22h. The resulting solution was evaporated and the dark oily residue flash-chromatographed over silica (33% $CH_2Cl_2$ in hexane) to give a green gum which was triturated with pet. ether (b.p. 40/60) to yield 1,2,5,6-tetrahydro-1,1,-dimethyl-6'-piperidinospiro [4H-pyrrolo[3,2,1-ij]quinoline-2,3'-[3H]naphth[2,1-b][1,4]oxazine] as an off-white solid (0.09 g;2%). mp 186° C.

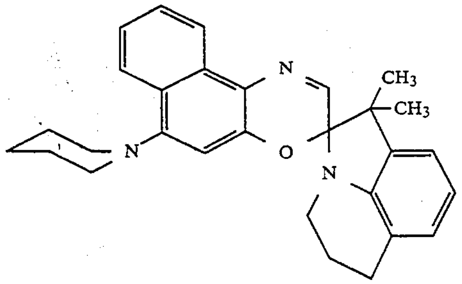

EXAMPLES 3-6

The compounds listed below as examples 3-6 were made by a process analogous to those described in Examples 1 and 2; the melting point obtained.

EXAMPLE 3

1,2,5,6-tetrahydro-1,1,4-trimethyl-6'-(p-diethylaminophenyl) spiro[4H-pyrrolo[3,2,1-ij]quinoline-2,3'-[3H]naphth[2,1-b][1,4]oxazine].

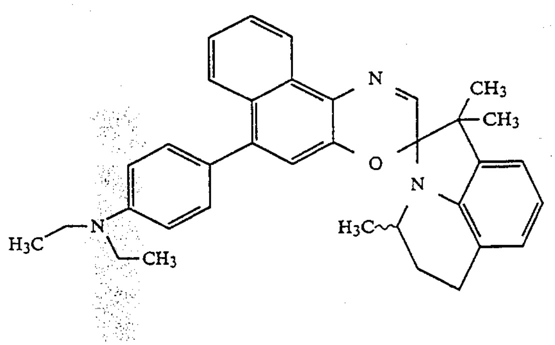

EXAMPLE 4

1,2,4,5-tetrahydro-1,1,4-trimethyl-6-(2,3 dihydroindol-1-yl) spiro[pyrrolo[3,2,1-hi]indoline-2,3 [3H]naphth[2,1-b][1,4]oxazine]. mp 207°–8° C.

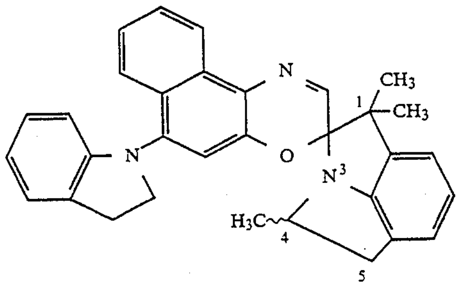

EXAMPLE 5

1,2,5,6-tetrahydro-1,1,-dimethylspiro[4H-pyrrolo[3,2,1-ij]quinoline-2,3'-[3H]naphth[2,1-b][1,4oxazine]. mp 163°–5° C.

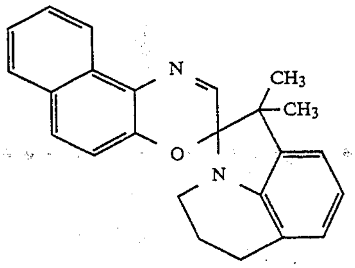

EXAMPLE 6

1,2,5,6-tetrahydro-1,1,4-trimethyl-6'-(2,3-dihydroindol-1-yl ) spiro[4H-pyrrolo[3,2,1-ij]quinoline-2,3'-[3H]naphth[2,1-b][1,4]oxazine]. mp 214°–7° C.

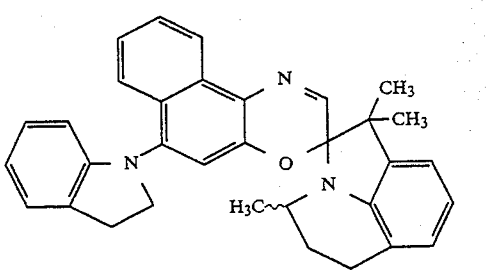

We claim:

1. Photochromic compounds having the following structure II

II

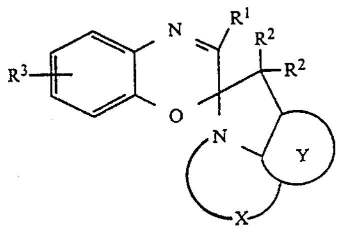

in which $R^1$ is a group selected from hydrogen, alkyl, alkoxy or amino;

each $R^2$ is a group selected from branched or linear-chain groups containing from 1 to 10 carbon atoms, a carboxylic group or a heterocyclic group or together form a carboxylic or heterocyclic ring;

$R^3$ is a group selected from hydrogen, alkyl, alkoxy, alkenyl, alkynyl, imino, azo, amino, carboxy ester, amide, cyano, halogen, trifluoromethyl, nitro, substituted or unsubstituted phenyl, substituted or unsubstituted pyridyl, or a fused carbocyclic or heterocyclic moiety;

Y is a six membered carbocyclic or heterocyclic ring.

X links N as shown to the ring Y to form a fused heterocyclic ring, said x-linkage containing 2 to 4 carbon atoms.

2. Photochromic compounds as claimed in claim 1 having the structure III in which $R^l$ is hydrogen;

each $R^2$is a group selected from branched or linear-chain alkyl group containing from 1 to 10 carbon atoms, a carbocyclic group or a heterocyclic group or together form part of a carbocyclic or heterocyclic ring;

$R^3$is a group selected from alkyl, substituted or unsubstituted phenyl, substituted or unsubstituted pyridyl, alkoxy, alkenyl, alkynyl, imino, azo, cyano, amino, halogen, trifluoromethyl and nitro;

$R^4$is a group selected from alkyl, substituted or unsubstituted phenyl, substituted or unsubstituted pyridyl, alkoxy, alkenyl, alkynyl, imino, azo, cyano, amino, halogen, trifluoromethyl and nitro, or $R^4$ is a carbocyclic or heterocyclic group fused to the 4, 5 or 5, 6 position of the indoline;

X links N as shown to the 7 position on the indoline ring to form a fused heterocyclic ring, said X-linkage contains 2 to 4 carbon atoms.

3. A photochromic compound as claimed in claim 2 wherein:

$R^1$ is hydrogen;

$R^2$ is a branched or linear alkyl group containing from 1 to 10 carbon atoms;

$R^3$ is selected from the group consisting of hydrogen, a branched or linear alkyl group containing from 1 to 4 carbon atoms, an alkoxy group containing from 1 to 4 carbon atoms, an amino group, a halogen atom, a trifluoromethyl group, a substituted or unsubstituted aryl group and an aryl substituted alkenyl group; and $R^4$ is selected from the group consisting of a branched or linear alkyl group containing from 1 to 4 carbon atoms, an alkoxy group containing from 1 to 4 carbon atoms, an amino group, a halogen atom, a trifluoromethyl group, a cyano group or a nitro group.

4. A compound as claimed in claim 3 in which the $R^3$ substituent is a substituted or unsubstituted phenyl group.

5. 1,2,5,6-tetrahydro-1,1,4-trimethyl-6'-(2,3-dihydroindol-1-yl)s piro[4H-pyrrolo[3,2,1-ij]quinoline-2,3'-[3H]naphth [2,1-b][1,4]oxazine].

6. A photochromic compound as claimed in claim 1 wherein at least one of the x-linkage carbon atoms is substituted.

7. A photochromic compound as claimed in claim 6 wherein the X-linkage further includes at least one nitrogen atom.

8. 1,2,5,6-tetrahydro-1,1,-dimethyl-6'-(2,3-dihydroindol-1-yl)spiro[4H-pyrrolo[3,2,1-ij]

9. 1,2,5,6-tetrahydro-1,1,-dimethyl-6'-piperidinospiro[4H-pyrrolo [3,2,1-ij ]quinoline-2,3'-[3H ]naphth[2,1-b][1,4 ]oxazine ].

10. 1,2,5,6-tetrahydro-1,1,4-trimethyl-6'-(p-diethylaminophenyl) spiro[4H-pyrrolo[3,2,1-ij ]quinoline-2,3'-[3H ]naphth[2,1-b][1,4 ]oxazine ].

11. 1,2,4,5-tetrahydro-1,1,4-trimethyl-6- (2,3 dihydroindol-1-yl ) spiro [pyrrolo [3,2,1-hi ]indoline-2,3 [3H ]naphth[2,1-b][1,4 ]oxazine ].

12. 1,2,5,6-tetrahydro-1,1,-dimethylspiro[4H-pyrrolo[3,2,1-ij ]quinoline-2,3'-[3H]naphth[2,1-b][1,4 ]oxazine ].

* * * * *